(12) United States Patent
Kagan

(10) Patent No.: US 10,517,185 B2
(45) Date of Patent: Dec. 24, 2019

(54) MODULAR DEVICE

(71) Applicant: Eugen Kagan, Niederkassel Lülsdorf (DE)

(72) Inventor: Eugen Kagan, Niederkassel Lülsdorf (DE)

( * ) Notice: Subject to any disclaimer, the term of this patent is extended or adjusted under 35 U.S.C. 154(b) by 0 days.

(21) Appl. No.: 15/889,712

(22) Filed: Feb. 6, 2018

(65) Prior Publication Data

US 2018/0228044 A1    Aug. 9, 2018

(30) Foreign Application Priority Data

Feb. 8, 2017    (DE) .................. 10 2017 102 503

(51) Int. Cl.

| | |
|---|---|
| *H05K 7/02* | (2006.01) |
| *H05K 5/02* | (2006.01) |
| *G01D 5/14* | (2006.01) |
| *G01D 5/26* | (2006.01) |
| *A61G 12/00* | (2006.01) |
| *G16H 40/63* | (2018.01) |
| *A61B 5/0402* | (2006.01) |
| *G06F 9/44* | (2018.01) |

(52) U.S. Cl.
CPC ............. *H05K 7/023* (2013.01); *A61G 12/00* (2013.01); *G01D 5/145* (2013.01); *G01D 5/26* (2013.01); *G16H 40/63* (2018.01); *H05K 5/0221* (2013.01); *H05K 5/0286* (2013.01); *A61B 5/0402* (2013.01); *G06F 9/44* (2013.01)

(58) Field of Classification Search
CPC .... H05K 7/023; H05K 5/0221; H05K 5/0286; A61N 1/3968; G16H 40/63; G01D 5/145; G01D 5/26; A61G 12/00; A61B 5/0402; G06F 9/44; G06F 19/00

USPC ......................................................... 361/735
See application file for complete search history.

(56) References Cited

U.S. PATENT DOCUMENTS

| | | | |
|---|---|---|---|
| 4,313,150 A * | 1/1982 | Chu ..................... | H05K 7/1409 361/755 |
| 2006/0221582 A1* | 10/2006 | Denies ................. | H05K 7/1409 361/752 |
| 2010/0109655 A1* | 5/2010 | Tanaka .................. | G01D 5/145 324/207.25 |
| 2013/0107424 A1* | 5/2013 | Thomas ............... | H05K 7/1411 361/679.01 |

FOREIGN PATENT DOCUMENTS

| | | |
|---|---|---|
| DE | 10 2012 103 029 A1 | 10/2013 |
| DE | 10 2015 117 581 A1 | 4/2017 |
| WO | WO 2015/094248 A1 | 6/2015 |

* cited by examiner

*Primary Examiner* — Rockshana D Chowdhury
(74) *Attorney, Agent, or Firm* — Pauley Erickson & Kottis

(57) ABSTRACT

A modular device, including a base unit with a plurality of module sockets and a number of modules that can be detachably connected to the module socket as well as a control unit for the connected modules, and the module sockets have manually actuatable locking devices for the modules. The locking devices include a manually actuated actuating device, which can be pivoted around a pivot axis from a first end position through an intermediate position into a second end position and which locks the module in the first end position and release the module in the second end position, and have a detector for detecting at least the first end position and the intermediate position of the actuating device.

14 Claims, 3 Drawing Sheets

MODULAR DEVICE

BACKGROUND OF THE INVENTION

Field of the Invention

This invention relates to a modular device such as an intensive care medical device.

Discussion of Related Art

Known modular devices include a base unit with a plurality of module sockets and a number of modules that can be detachably connected to the module sockets and a control unit for the connected modules. The module sockets can be equipped with manually actuable locking devices for the modules. In the intensive care field, modular devices of this kind are known, for example, from German Patent Reference DE 10 2012 103029 A1 and permit the base unit, which makes it possible to operate and control all of the modules, to be equipped with different function modules depending on patient needs. The modules can be quickly and flexibly connected to and removed from the base unit and can be replaced with simple movements.

The locking of the modules in the region of the respective module sockets of the base unit, however, must meet strict mechanical requirements, for example with regard to vibration-proofness and impact resistance, particularly when using such a modular device in a mobile or emergency medical context. It is necessary to ensure that a module, which is needed for checking a patient's vital functions, is not inadvertently removed or inadvertently destroyed when released from the module socket or is not reduced in its functionality, for example due to an abrupt interruption of a software program that is running. The signal transmission of individual contacts, such as in the form of pins between the base unit and the modules, must not be interrupted under any circumstances and the connection should be carried out in a rattle-free and vibration-free way and must be easy to lock and unlock. In a drop test, the components must be fracture-resistant and in addition, a seal preventing the penetration of moisture, such as defined in IP 54, must be ensured.

One object of this invention is to provide a modular device of the type mentioned above, whose locking devices are easy to operate by hand, but permit a stable locking of the module in the module socket and are prevented from being incorrectly operated. The modular device also ensures a complete, function-retaining shut-down of a module before its removal from the module socket of the base unit.

SUMMARY OF THE INVENTION

This object and others are attained according to this invention by a modular device according to features of different embodiments and modifications of this invention described in this specification and in the claims.

This invention provides locking devices that include a manually actuated fastening element, which can be pivoted around a pivot axis from a first end position through an intermediate position into a second end position and which locks the module in the first end position and releases the module in the second end position. In addition, a detector or detecting means are provided for detecting at least the first end position and the intermediate position of the actuating device. The actuating device can be embodied so that by an operator action, it can at first be pivoted only from the first end position into the intermediate position and from there, by a second operator action, can be pivoted further into the second end position. The movement of the actuating device from the first end position that locks the module into the second end position that releases the module therefore cannot occur in one step by an operator action. Instead, after the intermediate position that still locks the module, a second operator action must be deliberately executed in order to finally achieve the release by reaching the second end position. This effectively prevents the module from being inadvertently released. Also, according to this invention, the detector or detecting means can communicate with the control unit so that when the actuating device is pivoted from the first end position in the direction of the intermediate position, the control unit can output an alarm and when the actuating device is pivoted further in the direction toward the second end position, the control unit can switch off the module. The alarm can only be triggered when the module is active and switched on, otherwise, a corresponding warning message can be output when the module is inactive.

After the first operator action has been performed and the intermediate position has been reached, an operator can issue a deliberate acknowledgment by executing the second operator action in the direction toward the second end position. During this time, the control unit can then properly switch off the module that has been deliberately released by the operator, for example by shutting down the software, performing a log-off procedure, and switching off the power supply.

But if the first operator action toward the intermediate position occurred inadvertently, then the operator, also in light of the immediately triggered alarm, which can be carried out for example optically and/or acoustically, will not execute the required second operator action, but will instead return the actuating device back to the first end position, which stops the alarm. Because the module has not been released from the module socket on the base unit and has also not been switched off during this entire time in which the actuating device is being moved from the first end position to the intermediate position and back into the first end position again, the function of the relevant module, which may possibly be vital to the patient, remains uninterrupted. For at least this reason, the modular device according to this invention achieves an extremely high functional reliability even in terms of preventing incorrect operation, which takes into account the requirements of a medical device. However, a corresponding embodiment of the actuating device makes it possible for the modules to be locked to the base unit and released from it in a simple way.

According to one embodiment of this invention, the actuating device comprises a disk that is supported so that it is able to rotate around the pivot axis and that has two engagement recesses for a finger of an operator, which extend radially inward and are separated from each other by an intermediate piece, and the actuating device is positioned adjacent to a module socket so that in the first end position, a first engagement recess is accessible from the outside and by a finger engagement in this first engagement recess, a pivoting into the intermediate position is enabled while the second engagement recess remains covered and in the intermediate position, the second engagement recess is accessible from the outside and by a finger engagement in the second engagement recess, a pivoting of the disk into the second end position is enabled.

This embodiment provides an operator with a predetermined required sequence of operating steps, namely engagement of a finger in the first engagement recess and pivoting of the disk from the first end position into the intermediate position, thus triggering an alarm, and then another engagement of a finger in the second engagement recess, which is only accessible in the intermediate position, which permits a pivoting into the second end position. Such an execution of a plurality of steps while an alarm is triggered is reliably prevented from occurring inadvertently and conversely is embodied in such a simple way that it can be intuitively performed, even under stressful conditions.

According to one embodiment of this invention, the locking devices include a locking opening in the region of the module sockets of the base unit and the modules have a hook that can be inserted into the locking opening, with the actuating device being shaped so that outside the second end position, it engages in locking fashion behind the protruding hook of the module in the locking opening. In this regard, the actuating device is used not only to perform the necessary movements for locking and releasing a module, but also forms or constitutes the actual locking and releasing mechanism for the modules, which significantly reduces the structural complexity and the number of parts required.

The detecting means or detector provided as part of the invention can, for example include magnetic, optical, or electrical sensors and/or contacts. In particular, magnetic detecting means in the form of Hall sensors are provided, which cooperate with magnet elements with which the actuating device is equipped so that the Hall sensors can detect these magnet elements and can correspondingly detect the respective position of the actuating device and as a function thereof, can trigger alarm functions and shutdown functions of the control unit for the relevant module.

According to one possible embodiment of this invention, a switching lug is allocated to the actuating device. This lug can be pivoted together with it around the pivot axis and supports the magnet elements in the unambiguous orientation and arrangement that are required for the function.

To further increase the functional reliability of the modular device according to this invention and its resistance to incorrect operation, in the first and second end positions and in the intermediate position, the actuating device detachably engages in them in detent fashion and, between the first end position and the intermediate position, is prestressed in the direction toward the first end position and, between the intermediate position and the second end position, is prestressed in the direction toward the intermediate position. In the event of an incorrect or inadvertent actuation of the actuating device, it automatically returns to the function-retaining state and a tactile feedback is produced for the operator.

BRIEF DESCRIPTION OF THE DRAWINGS

Other embodiments and details of this invention are explained in greater detail below based on the drawings, which show an exemplary embodiment, wherein.

DETAILED DESCRIPTION OF THE INVENTION

Figure 1:
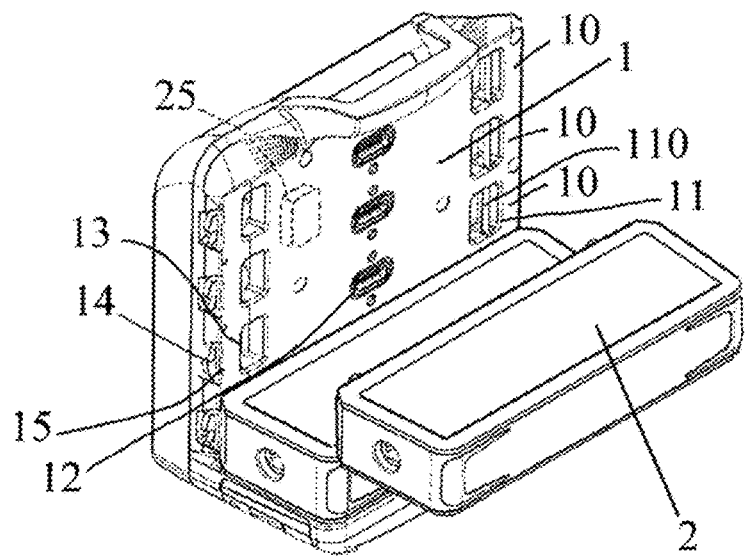
FIG. 1 is a perspective view of a modular device according to this invention.
Figure 2:
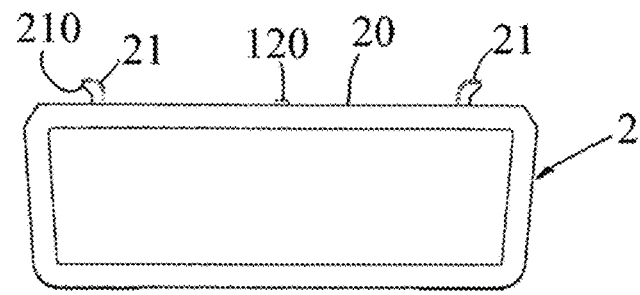
FIG. 2 is a top view of a module according to the modular device shown in FIG. 1.

FIG. 1 shows a modular device in the form of a modular medical device for intensive care that is used for stationary and mobile care of a patient. It includes a base unit labeled with the reference numeral 1 equipped with a plurality of identically embodied module sockets 10 arranged one on top of another to which individual modules 2 can be detachably connected in a way that will be described in greater detail below in order to additionally provide the base unit 1 with additional functions that are required for treating the patient in the respective instance of use. Examples of such functions that can be integrated into individual modules 2 include artificial respiration, EKG diagnosis, and a multitude of other intensive care functions, which are not subject to any general limitation.

In a way not shown in greater detail, the base unit 1 in this case includes not only a power supply for mobile operation of both the base unit 1 and the connected modules 2, but also a control unit 25 that can control the connected modules in the desired way and can process and display data sent by the modules, for example vital data of patients. A touch-screen monitor that is not shown in FIG. 1 is provided for this purpose on the front side of the base unit 1.

Approximately in the middle region, each module socket 10 has a connector panel 12 for electrically contacting the module 2 that can be fastened to the module socket 10. Each module 2 can be equipped with a contact element 120 that corresponds to this on the side 20 facing the module socket 10. As shown in FIG. 1, on the right side of each module socket 10, a latching opening 11 is provided, which contains a vertically extending latching element 110. Correspondingly, on the left side of each module socket 10 in FIG. 1, another locking opening 13 is provided in the base unit 1, in which an actuating device 14, which can be accessed from the outside by hollows 15 in the narrow side of the base unit 1, depending on the positioning of the actuating device 14, engages or releases the locking opening 13. Thus, each module is correspondingly provided with protruding hooks 21 on the side 20 facing the module socket, which engage in the latching and locking opening 13 and engage behind the latching element 110 and the actuating device 14 that protrudes into the locking opening 13. This produces a reliable attachment of the module 2 to a module socket 10. Because of the selected configuration of each module 2, docking can also occur in an orientation that is rotated by 180°, for example in order to route lateral connecting terminals to the right or left side of the modular device as a function of accessibility.

Figure 3:
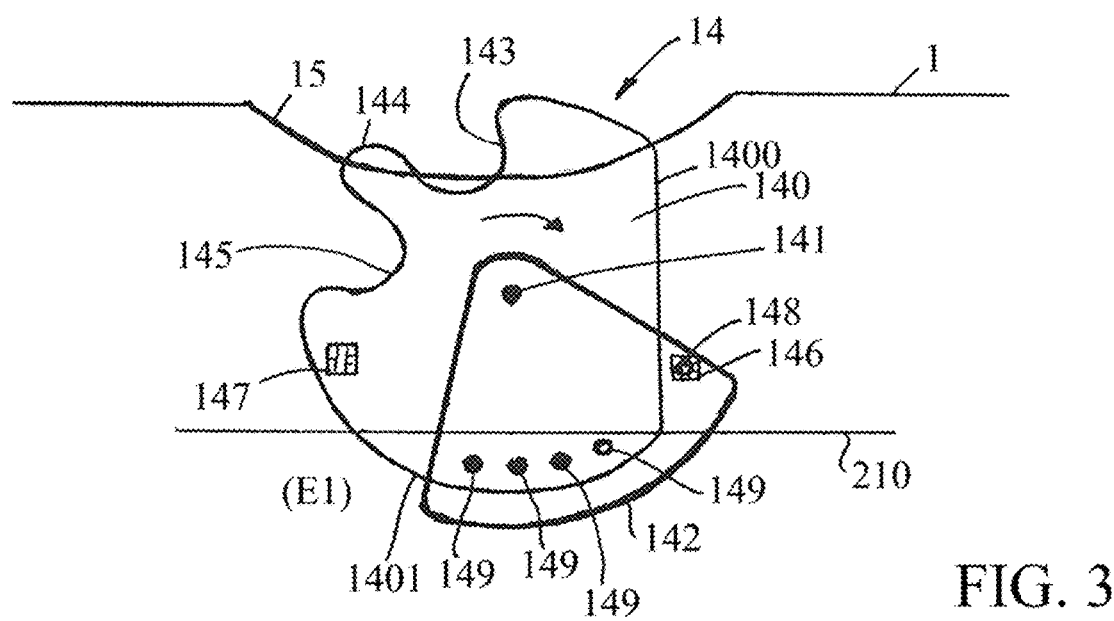
FIG. 3 is a schematic view of the actuating device according to this invention, in a first end position.
Figure 4:
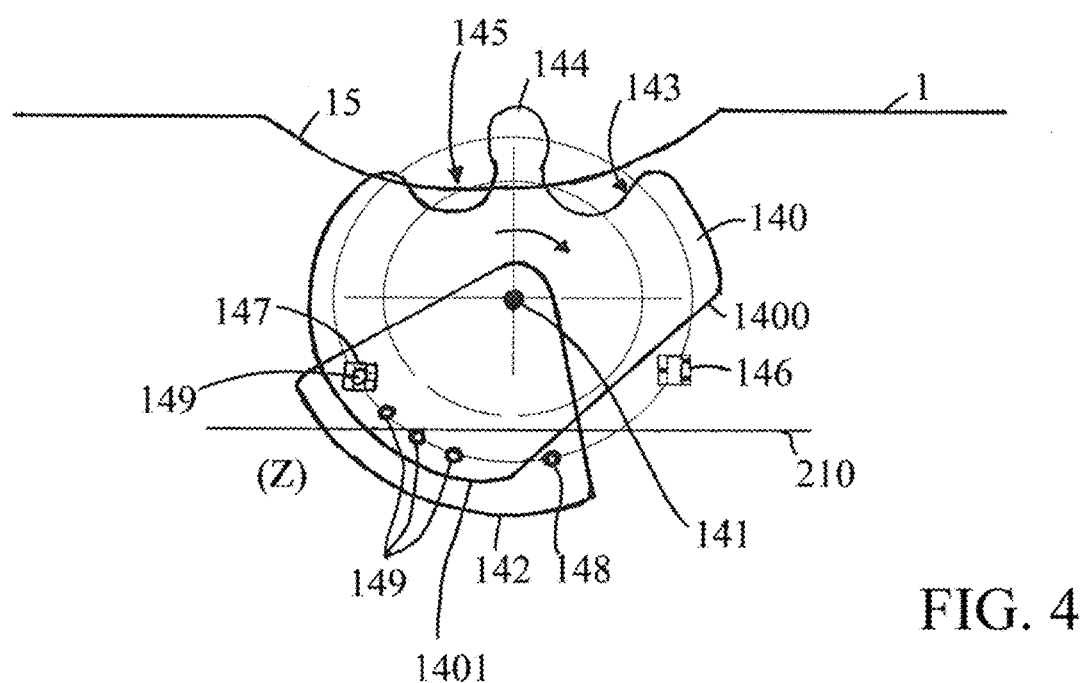
FIG. 4 is a schematic view of the actuating device according to this invention, in an intermediate position.
Figure 5:
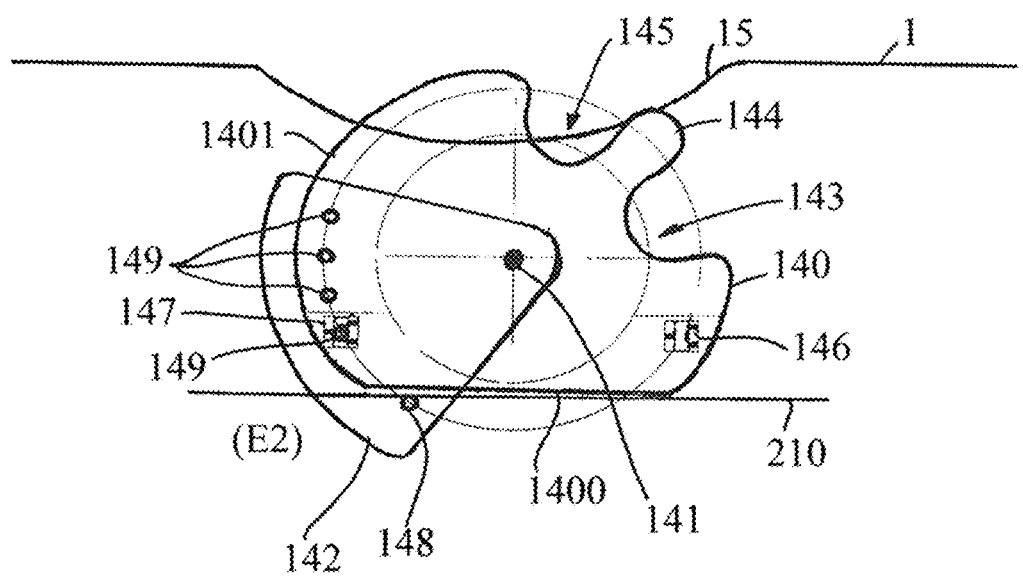
FIG. 5 is a schematic view of the actuating device according to this invention, in a second end position.

The design and function of the actuating device 14 are shown in greater detail by the schematic views of FIGS. 3-5, which show the actuating device in cooperation with a module 2 that is connected to the module socket 10 in various positions and states.

FIG. 3 shows the actuating device 14 in a first end position E1 in which the fastening element 14 securely locks the docked module 2 in the region of or near the hook 21 that engages in the locking opening 13, which thus constitutes or forms the normal operating state of a module 2 that is docked to the base unit 1. Naturally, the opposing hook 21 likewise engages behind the latching element 110 inside the latching opening 11.

As shown in FIG. 1, the actuating device 14 is produced from the basic shape of a disk 140, which can be accessed from the outside via the lateral finger hollow 15 on the base unit 1 in the way that is described in greater detail below so that it can be actuated, for example, by an operator's finger that is not shown in the drawing. The disk 140 can be pivoted around a pivot axis 141 extending horizontally in the direction indicated by the arrow, for which purpose the disk 140 has a first engagement recess 143, which is machined into it in a radially inward direction and is accessible from the outside via the finger hollow 15 in the first end position E1 shown. An intermediate piece 144 divides this from a second engagement recess 145, but the latter recess comes to rest inside the housing of the base unit 1 in the shown first end position E1 and is thus not accessible from the outside via the finger hollow 15.

In its side radially opposite from the engagement recess 143 relative to the pivot axis 141, a region of the disk 140 that is labeled with the reference numeral 1401 is positioned so that it engages behind the shown free end 210 of the hook 21 and thus locks it onto the module socket 10 in the above-described way.

Connected rigidly to the disk 140 and thus able to pivot with it around the pivot axis 141, a switching lug 142 is provided, which supports four magnets 149 that are arranged approximately equidistantly from one another and positioned on a segment of the same circle extending around the pivot axis 141 and spaced somewhat farther apart from them, an additional magnet is provided with the reference numeral 148. Furthermore, in the region 2 across which the pivotable disk 140 and the switching lug 142 can sweep during a pivoting movement, detecting means or a detector in the form of stationary Hall sensors 146, 147 are provided, which are positioned so that in the shown first end position E1, the magnet 148 on the switching lug 142 is positioned over the Hall sensor 146 and can thus be detected by the latter whereas the other magnets 149 cannot be detected and registered by either the Hall sensor 146 or the additional Hall sensor 147 because they are spaced a corresponding distance apart from them. Consequently, if the Hall sensor 146 detects a magnet, in this case the magnet 148, then this state is unambiguously associated with the positioning of the actuating device 14 in the first end position E1 according to FIG. 3 and can be signaled to the control unit as a normal operating state with a locked module 2, in which the module 2 can be used as intended.

FIGS. 4 and 5 in succession with each other show how such a module 2 that is locked according to FIG. 3 can be disconnected from the base unit 1 and removed after being released.

Thus, as already explained in connection with FIG. 3, by means of or with a finger engagement in the first engagement recess 143, the disk 140 serving as an actuating device 14 is pivoted clockwise around the pivot axis 141 in accordance with the arrow shown in FIG. 3 until it assumes the intermediate position Z shown in FIG. 4 in which the first engagement recess 143 disappears into the housing of the base unit 1 and is then no longer accessible for further actuation.

In this shown intermediate position Z, the section of the disk 140 provided with the reference numeral 1401 still locks the free end 210 of the hook 21, but the magnet 148 positioned on the switching lug 142 is no longer situated or positioned above the Hall sensor 146 and as a result, is also no longer detected by it. As an immediate result, the Hall sensor 146 sends a corresponding signal to the control unit, which in turn outputs an optical and/or acoustic alarm. Furthermore, in the shown pivot position, the first of the four magnets 149 in one embodiment travels into in the detection range of the opposing additional Hall sensor 147, which is likewise signaled to the control unit. In addition to the alarm triggered by means of or with the Hall sensors 146, the control unit which is triggered by the Hall sensor 147 can thus initiate a switching-off procedure of the module, which is still locked, for example by shutting down the software that is running on it.

The output of the alarm by the Hall sensor 146 notifies the operator that the intermediate position Z has been reached. The operator can then check whether the switching-off procedure was intentional and wanted or was initiated inadvertently. If the switching procedure was initiated inadvertently, then the actuating device 14 can be immediately moved back into the first end position shown in FIG. 3 in which the alarm stops and the normal state for the module 2 is brought about, without having interrupted its locking at any point in time.

But if achievement of the intermediate position Z and the outputting of the alarm are attributed to a deliberate actuation by the operator, then in order to release the module 2 that is already in the process of the shut-down procedure, the operator must deliberately withdraw the finger used from the first engagement recess 143 and insert it behind the intermediate piece 144, into the now accessible second engagement recess 145 in order to move the disk 140 further in the pivoting direction according to the depicted arrow, into the second end position E2 shown in FIG. 5.

In this second end position E2 shown in FIG. 5, the Hall sensor 147 still detects one of the in this case four magnets 149 that are spaced equidistantly from one another. The distance between the adjacent magnets 149 is chosen so that during the entire pivoting movement of the disk 140 from the intermediate position Z according to FIG. 4 to the second end position E2 according to FIG. 5, they are always continuously detected by the Hall sensor 147 across its hysteresis range. In this regard, instead of several individual magnets 149 that are spaced equidistantly apart from one another, it is also possible for a corresponding continuous magnet to be provided in this region of the switching lug 142. The continuous detection of a magnet with the Hall sensors 147 ensures that the module 2 is completely switched off before the second end position of the disk 140 shown in FIG. 5 is reached.

It is also clear that near or adjacent to the section 1401 of the disk 140, a disk segment is cut off along a straight release edge 1400, which in the second end position E2, extends parallel to the free end 210 of the protruding hook 21 of the module 2, but no longer engages behind it so that in this shown second end position E2, the hook 21 of the module 2 is released and the module 2 can be removed from the base unit 1.

The fastening and docking of a module 2 to one of the module sockets 10 consequently takes place in the reverse order.

To further increase fail-safety and to produce a tactile feedback, the disk serving as an actuating device 14 can be detachably engaged in decent fashion in the end positions E1 and E2 and in the intermediate position Z and, between the end position E1 and the intermediate position Z, is prestressed in the direction toward the end position E1. In the same way, a prestressing in the direction of the intermediate position Z can also be provided between the intermediate position Z and the second end position E2.

By the shown embodiment of the actuating device 14, the modular device explained above achieves a particularly simple, fail-safe, and incorrect operation-preventing locking and release of the modules 2 that can be optionally fastened to the base unit 1, which meet the requirements of a medical device with a life-sustaining functionality.

German Patent Reference DE 10 2017 102 503.0, filed 8 Feb. 2017, the priority document corresponding to this invention, to which a foreign priority benefit is claimed under Title 35, United States Code, Section 11.9, and its entire teachings are incorporated, by reference, into this specification.

What is claimed is:

1. A modular device, including a base unit (1) with a plurality of module sockets (10) and modules (2) detachably connectable to the plurality of module sockets (10) and a control unit for the modules (2), the plurality of module sockets (10) having locking devices for the modules (2) and that are each manually actuatable, the modular device comprising: the locking devices including an actuating device which is manually pivotable around a pivot axis (141) from a first end position (E1) through an intermediate position (Z) into a second end position (E2) and which locks the modules (2) in the first end position (E1) and releases the modules (2) in the second end position (E2) and having a detector for detecting at least the first end position (E1) and the intermediate position (Z) of the actuating device, the actuating device by an operator action is first pivoted only from the first end position (E1) into a standstill at the intermediate position (Z) and from the standstill, by a second operator action is pivoted further into the second end position (E2), and the detector communicating with the control unit so that when the actuating device is pivoted from the first end position (E1) in a direction of the intermediate position (Z), the control unit outputs an alarm and when the actuating device is pivoted further in the direction toward the second end position (E2), the control unit switches off the modules (2);

wherein the actuating device is of a disk (140) that is supported to rotate around the pivot axis (141), the disk is accessible from outside via a lateral finger hollow (15) on the base unit (1), and has the disk two engagement recesses (143,145) for a finger, which extend radially inward and are separated from each other by an intermediate piece (144), and the actuating device is positioned near a corresponding one of the plurality of module sockets (10) so that in the first end position (E1) a first engagement recess (143) is accessible from the outside and by a finger engagement in the first engagement recess (143), a pivoting into the intermediate position (Z) is enabled while the second engagement recess (145) is covered and in the intermediate position (Z), the second engagement recess (145) is accessible from the outside and by a finger engagement in the second engagement recess (145) so that a pivoting of the disk (140) into the second end position (E2) is enabled.

2. The modular device according to claim 1, wherein the locking devices have a locking opening (13) near the plurality of module sockets (10) of the base unit (1) and the modules (2) have a hook (21) insertable into the locking opening (13) and the actuating device shaped so that outside the second end position (E2) the actuating device engages in locking fashion behind the hook (21) of the modules (2) in the locking opening (13).

3. The modular device according to claim 2, wherein the detector includes magnetic or optical sensors.

4. The modular device according to claim 3, wherein a magnetic detector formed as Hall sensors (146, 147) and the actuating device has a plurality of magnet elements (148, 149) detected by the Hall sensors (146, 147).

5. The modular device according to claim 4, wherein a switching lug (142) is allocated to the actuating device and pivot together around the pivot axis (141) and supports the magnet elements (148, 149).

6. The modular device according to claim 5, wherein in the first and second end positions (E1, E2) and in the intermediate position (Z), the actuating device detachably engages in a detent fashion and, between the first end position (E1) and the intermediate position (Z), is prestressed in a direction toward the first end position (E1) and, between the intermediate position (Z) and the second end position (E2), is prestressed in a direction toward the intermediate position (Z).

7. The modular device according to claim 6, wherein before the modules (2) is switched off, the control unit is able to shut down a software program running on the modules (2).

8. The modular device according to claim 1, wherein each of the locking devices includes a locking opening (13) near a corresponding one of the plurality of module sockets (10) of the base unit (1) and each of the modules (2) includes a hook (21) insertable into the locking opening (13) and the actuating device shaped so that outside the second end position (E2) the actuating device engages in locking fashion behind the hook (21) of the modules (2) in the locking opening (13).

9. The modular device according to claim 1, wherein the detector includes magnetic or optical sensors.

10. The modular device according to claim 9, wherein a magnetic detector formed as Hall sensors (146, 147) and the actuating device has a plurality of magnet elements (148, 149) detected by the Hall sensors (146, 147).

11. The modular device according to claim 10, wherein a switching lug (142) is allocated to the actuating device and pivot together around the pivot axis (141) and supports the magnet elements (148, 149).

12. The modular device according to claim 1, wherein in the first and second end positions (E1, E2) and in the intermediate position (Z), the actuating device detachably engages in a detent fashion and, between the first end position (E1) and the intermediate position (Z), is prestressed in a direction toward the first end position (E1) and, between the intermediate position (Z) and the second end position (E2), is prestressed in a direction toward the intermediate position (Z).

13. The modular device according to claim 1, wherein before a module (2) is switched off, the control unit is able to shut down a software program running on the module (2).

14. A modular device, comprising: a base unit (1) with a plurality of module sockets (10), modules (2) detachably connectable to the module sockets (10), and a control unit for the modules (2);

each of the plurality of module sockets (10) including a locking device for a corresponding one of the modules (2), the locking device including an actuating device manually pivotable around a pivot axis (141) from a first end position (E1) through an intermediate position (Z) into a second end position (E2) and which locks the corresponding one of the modules (2) in the first end position (E1) and releases the corresponding one of the modules (2) in the second end position (E2), wherein: the actuating device comprises a disk (140) that is supported to rotate around the pivot axis (141), the disk is accessible from outside via a lateral finger hollow (15) on the base unit (1), the disk has two engagement recesses (143, 145) each for a finger and each extending radially inward, and an intermediate piece (144) separating the two engagement recesses (143,145); the actuating device is positioned near a corresponding one of the plurality of module sockets (10) so that in a first end position (E1) a first engagement recess (143) is accessible from the outside and by a finger engagement in the first engagement recess (143); and the actuating device includes a second engagement recess (145) that is not accessible in the first end position (E1), and accessible upon rotation of the actuating device to the intermediate position (Z);

each of the plurality of module sockets (10) including a detector configured to detect at least the first end position (E1) and the intermediate position (Z) of the actuating device;

wherein the actuating device by an operator action is first pivoted only from the first end position (E1), where the second engagement recess (145) is covered, into the intermediate position (Z) where the second engagement recess (145) is accessible from the outside and enabling by a finger engagement in the second engagement recess (145) so that a pivoting of the disk (140) into the second end position (E2), and then by a second operator action on the engagement recess the intermediate piece (144) is pivoted further into the second end position (E2), and the detector communicating with the control unit so that when the actuating device is pivoted from the first end position (E1) in a direction of the intermediate position (Z), the control unit outputs an alarm and when the actuating device is pivoted further in a direction toward the second end position (E2), the control unit switches off the corresponding one of the modules (2).

* * * * *